United States Patent

Sudo et al.

[11] Patent Number: 6,129,712
[45] Date of Patent: Oct. 10, 2000

[54] PLUNGER FOR SYRINGE

[75] Inventors: Morihiro Sudo; Kouichi Asai, both of Tokyo, Japan

[73] Assignee: Daikyo Seiko, Ltd., Tokyo, Japan

[21] Appl. No.: 09/329,624

[22] Filed: Jun. 10, 1999

[30] Foreign Application Priority Data

Nov. 5, 1998 [JP] Japan .................................. 10-314193

[51] Int. Cl.⁷ .................................................. A61M 5/00
[52] U.S. Cl. ............................................ 604/218; 604/228
[58] Field of Search .................................. 604/218, 187, 604/219, 224, 228

[56] References Cited

U.S. PATENT DOCUMENTS

| | | | |
|---|---|---|---|
| 5,032,114 | 7/1991 | Olovson | 604/228 |
| 5,094,148 | 3/1992 | Haber et al. | 604/218 X |
| 5,460,617 | 10/1995 | Minkus et al. | 604/218 |
| 5,688,252 | 11/1997 | Matsuda et al. | 604/228 X |

*Primary Examiner*—John D. Yasko
*Attorney, Agent, or Firm*—McCormick, Paulding & Huber LLP

[57] ABSTRACT

In a plunger for a syringe including a laminated piston which is provided with a shaft with a female thread and which is slidably inserted into a barrel and a rod having a male thread which can be screw-engaged in the threaded hole of the laminated piston, the axial length T of the crest of the female thread and the root of the male thread which engages with the female thread is greater than the axial length t of the root of the female thread and the crest of the male thread.

6 Claims, 2 Drawing Sheets

PLUNGER FOR SYRINGE

BACKGROUND OF THE INVENTION

1. Field of the Invention

The present invention relates to a plunger for a syringe which is adapted to aspirate or eject a quantity of liquid medicament into or from a barrel of the syringe.

2. Description of the Related Art

In general, a plunger for a syringe is composed of a piston which is slidably inserted into a barrel and a rod which is screwed in a threaded hole (female hole) formed at the center of the piston. The entirety of the piston is usually made of rubber and is coated at its outer surface with silicone oil to reduce sliding resistance. In recent years, harmful influence of the silicone oil on humans has come into question. To solve this problem, the assignee of the present application has proposed a laminated piston which is made of a rubber piston having a laminated layer. The rubber piston is coated at its outer surface with the laminated layer made of a tetrafluoroethylene resin film, an ethylene-tetrafluoroethylene resin film, or a ultra high molecular weight polyethylene resin film.

However, the laminated piston exhibits a higher sliding resistance to the barrel than the conventional rubber piston coated with silicone oil. When in use, the laminated piston is pushed in the barrel (moved inward) to eject liquid medicament from the barrel, and is drawn (moved outward) to aspirate the liquid medicament into the barrel. In conventional products, when the rod (laminated piston) is drawn (moved outward), there is a possibility that the rod disengages or detaches from the laminated piston, due to the large sliding resistance between the laminated piston and the barrel. This is due to deformation of the threaded hole of the soft laminated piston in which the rod is screwed.

SUMMARY OF THE INVENTION

It is an object of the present invention to provide a plunger for a syringe using the same thread engagement structure as above, in which a rod cannot be drawn out from the piston.

In order to achieve the above-mentioned object, according to the present invention, there is provided a plunger for a syringe including a piston which is slidably inserted into a barrel and a rod connected to the piston, including: a female thread formed at the center of the piston; and a male thread which can be screw-engaged into the female thread of the piston; wherein the axial length T of the crest of the female thread and the root of the male thread which engages with the female thread is greater than the axial length t of the root of the female thread and the crest of the male thread. It has been discovered that the reason why the rod is disengaged from the laminated piston is that the axial length of the crest and root of the female thread and the male thread is identical to the axial length of the root and crest of the female thread and the male thread, so that the crest of the female thread of the laminated piston can be easily deformed. To prevent the rod from being disengaged from the laminated piston, the axial length of the crest of the female thread is greater than the axial length of the root of the female thread.

The present invention can be advantageously applied to a laminated piston which exhibits a higher sliding resistance to the barrel, the laminated piston composing a rubber piston and a laminated layer of synthetic resin which coats the outer surface of the rubber piston. Accordingly, silicone oil need not be used for lubrication of the sliding piston, as the synthetic resin allows sufficient slidable movement of the piston.

Preferably, the axial length T of the crest of the female thread and the root of the male thread which engages with the internal and the axial length t of the root of the female thread and the crest of the male thread satisfies the following condition: T>1.2t.

Preferably, the axial length T of the crest of the female thread and the root of the male thread which engages with the internal and the axial length t of the root of the female thread and the crest of the male thread satisfies the following condition: T>1.5t.

Preferably, the rubber piston of the laminated piston is made from one of the following: IIR, NBR, BR, or EPDM.

Preferably, the laminated film layer of the laminated piston is made of a resin material selected from the following: tetrafluoroethylene, ethylene-tetrafluoroethylene, and ultra high molecular weight polyethylene.

The present disclosure relates to subject matter contained in Japanese Patent Application No. 10-314193 (filed on Nov. 5, 1998) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 3:
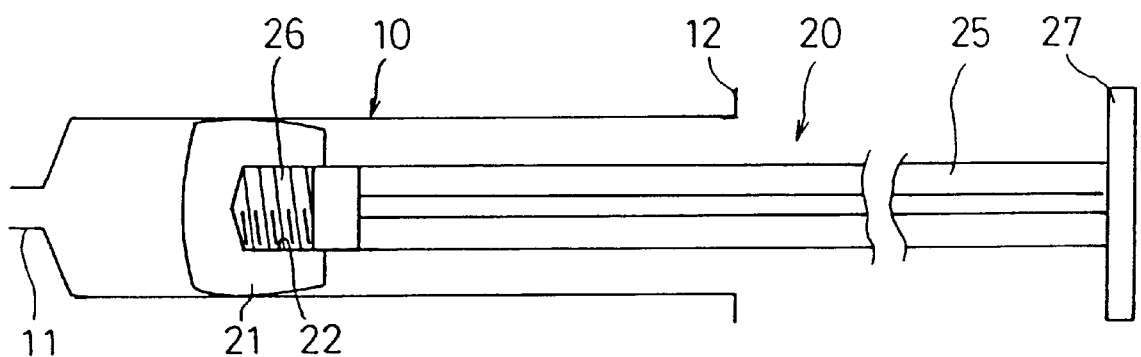
FIG. 3 is a sectional view of a plunger fitted into a barrel of a syringe.

As can be seen in FIG. 3, a syringe is composed of a barrel 10 and a plunger 20. The barrel 10 is provided on its front end with a needle mounting nozzle 11 and on its rear end with a finger flange 12.

The plunger 20 is composed of a laminated piston 21 which is slidably fitted into the barrel 10 and a rod 25 which is screw-engaged into the laminated piston 21. The laminated piston 21 is made of a rubber piston 21a which is coated at its outer surface with a laminated layer (film) 21b of synthetic resin. The rubber piston 21a is provided at the center thereof with a blind threaded-hole (female thread) 22. The rod 25 is provided, on its tip end, with a threaded portion (male thread) 26 which can be screw-engaged into the threaded hole 22, and on its rear end, with a pressure flange (thumb rest) 27. The laminated film 21b is made of a resin material selected from tetrafluoroethylene, ethylene-tetrafluoroethylene, and ultra high molecular weight polyethylene.

Figure 1:
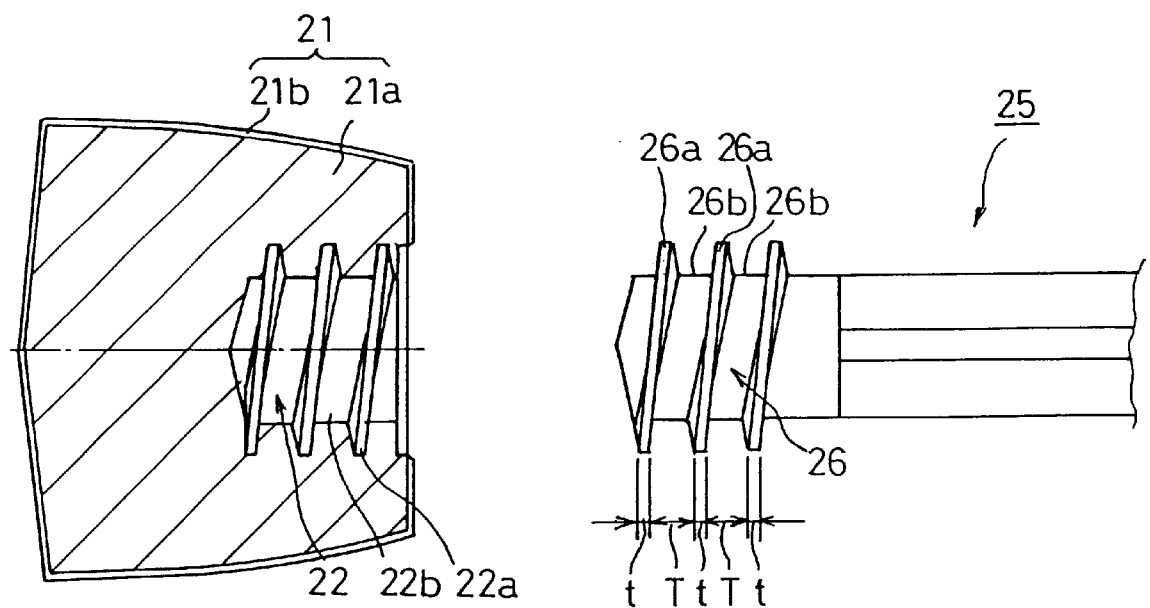
FIG. 1 is a partially sectioned, enlarged side view of a laminated piston and a rod for a plunger in a syringe, according to an embodiment of the present invention.
Figure 2:
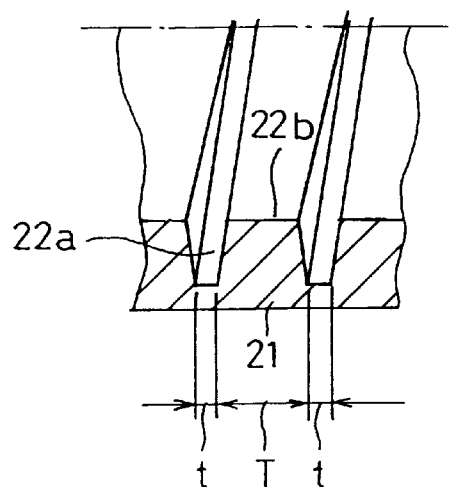
FIG. 2 is an enlarged sectional view of a threaded hole (female thread) of a laminated piston shown in FIG. 1.

The shape of the female thread (threaded hole) 22 of the laminated piston 21 and the male thread 26 of the rod 25 is shown in FIGS. 1 and 2. The threaded hole 22 is defined by alternately located spiral root 22a and spiral crest 22b (defined by a spiral root 22a). The male thread 26 is defined by alternately located spiral crest 26a and spiral root 26b (defined by a spiral crest 26a), corresponding to the spiral root 22a and the spiral crest 22b, respectively. In the illustrated embodiment, the thread is a double thread.

According to the significant feature of the present embodiment, the axial lengths of the root 22a and the crest 22b of the female thread 22 (crest 26a and root 26b of the male thread 26) are different. Namely, the axial length "t" of the root 22a (crest 26a) and the axial length "T" of the crest 22b (root 26b) satisfy the following relationship: T>t.

If the axial length "T" of the crest 22b of the female thread 22 (root 26b of the male thread 26) is greater than the axial length "t" of the root 22a of the female thread 22 (crest 26a of the male thread 26), no deformation of the crest 22b of the laminated piston 21 tends to occur. Consequently, if a force in a direction to draw the rod 25 from the barrel 10 is applied to the rod, no unintended disengagement of the rod from the laminated piston 21 takes place.

The rubber piston 21a of the laminated piston 21 can be made of, for example, IIR, NBR, BR, or EPDM.

The axial lengths "T" and "t" are determined depending on the hardness (or softness) of the rubber of which the laminated piston 21 is made and preferably satisfy the following equation: T>1.2t; and more preferably T>1.5t.

There are various kinds of threads that can be utilized for the syringe, including a coarse thread, a fine thread, or a trapezoidal thread, etc. The thread used in the present invention is not limited to a specific thread.

As can be understood from the above discussion, in a plunger for a syringe including a laminated piston which can be slidably inserted into a barrel of the syringe and a rod which can be screw-engaged in the laminated piston, since the axial length T of the crest of the threaded hole and the root of the male thread of the laminated piston and the rod is greater than the axial length t of the root of the threaded hole and the crest of the male thread, when the rod is drawn from the barrel, no unintended disengagement of the rod from the laminated piston occurs.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A plunger for a syringe including a piston which is slidably inserted into a barrel and a rod connected to said piston, comprising:
    a female thread formed at the center of said piston; and
    a male thread which is screw-engaged into the female thread of the piston;
    wherein the axial length T of the crest of the female thread and the root of the male thread which engages with the female thread is greater than the axial length t of the root of the female thread and the crest of the male thread.

2. The plunger for a syringe according to claim 1, wherein said piston comprises a laminated piston, said laminated piston comprising a rubber piston and a laminated layer of synthetic resin which coats the outer surface of the rubber piston.

3. The plunger for a syringe according to claim 1, wherein the axial length T of the crest of the female thread and the root of the male thread which engages with the internal and the axial length t of the root of the female thread and the crest of the male thread satisfies the following condition: T>1.2t.

4. The plunger for a syringe according to claim 3, wherein the axial length T of the crest of the female thread and the root of the male thread which engages with the internal and the axial length t of the root of the female thread and the crest of the male thread satisfies the following condition: T>1.5t.

5. The plunger for a syringe according to claim 2, wherein said rubber piston of the laminated piston is made from one of the following: IIR, NBR, BR, or EPDM.

6. The plunger for a syringe according to claim 2, wherein said laminated film layer of the laminated piston is made of a resin material selected from the following: tetrafluoroethylene, ethylene-tetrafluoroethylene, and ultra high molecular weight polyethylene.

* * * * *